United States Patent

Whitehouse et al.

[11] Patent Number: 5,844,237
[45] Date of Patent: Dec. 1, 1998

[54] ELECTROSPRAY AND ATMOSPHERIC PRESSURE CHEMICAL IONIZATION SOURCES

[76] Inventors: Craig M. Whitehouse, 220 Pleasant Point Rd.; J. Fred Banks, Jr., 116 Limewood Ave., both of Branford, Conn. 06405; Clement Catalano, 30 Sunnybrook La., Clinton, Conn. 06413

[21] Appl. No.: 791,346

[22] Filed: Jan. 31, 1997

Related U.S. Application Data

[63] Continuation of Ser. No. 641,628, May 2, 1996, abandoned, which is a continuation of Ser. No. 208,632, Mar. 8, 1994, abandoned.

[51] Int. Cl.⁶ .............................. B01D 59/44; H01J 49/00
[52] U.S. Cl. ........................................... 250/288; 250/281
[58] Field of Search .................................. 250/281, 282, 250/288, 288 A

[56] References Cited

U.S. PATENT DOCUMENTS

| | | | |
|---|---|---|---|
| 4,209,696 | 6/1980 | Fite | 250/281 |
| 4,531,056 | 7/1985 | Labowsky et al. | 350/288 |
| 4,542,293 | 9/1985 | Fenn et al. | 250/288 |
| 4,861,988 | 8/1989 | Henion et al. | 250/288 |
| 5,051,583 | 9/1991 | Mimura et al. | 250/288 |
| 5,122,670 | 6/1992 | Mylchrest et al. | 250/288 |
| 5,130,538 | 7/1992 | Fenn et al. | 250/288 |
| 5,162,650 | 11/1992 | Bier | 250/288 |

*Primary Examiner*—Bruce Anderson
*Attorney, Agent, or Firm*—Levisohn, Lerner, Berger & Langsam

[57] ABSTRACT

Improvements have been made to the Electrospray and Atmospheric Pressure Chemical Ionization source chambers interfaced to mass spectrometers to simplify source performance optimization and source operation and to improve system sensitivity. The atmospheric pressure ion source procedure for optimizing performance has been simplified by adding windows along the sides of the atmospheric pressure ionization chamber allowing direct viewing of the Electrospray and Atmospheric pressure ion sources during operation. A cylindrical lens which extends along the side walls of the atmospheric pressure chamber has been configured to be semitransparent for viewing into the chamber. This cylindrical shaped side lens is electrically isolated from the Electrospray liquid introduction needle and Electrospray chamber endplate. Improved Electrospray mass spectrometer system sensitivity can be achieved when operating the cylindrical lens with a higher potential difference between it and the Electrospray liquid introduction needle than is set between the needle and the endplate.

22 Claims, 6 Drawing Sheets

ELECTROSPRAY AND ATMOSPHERIC PRESSURE CHEMICAL IONIZATION SOURCES

This application is a continuation of application Ser. No. 08/641,628 filed May 2, 1996 which application is now abandoned, and which is a continuation of application Ser. No. 08/208,632 filed Mar. 8, 1994, abandoned.

FIELD OF INVENTION

Atmospheric pressure ionization sources (API), in particular Electrospray (ES) and Atmospheric Pressure Chemical Ionization (APCI) sources, have expanded the range of applications to which mass spectrometric (MS) analysis is applied. Improved performance and the ability to operate the ES and APCI ion sources in simple and routine manner has contributed to widespread use of these API/MS techniques for routine as well as complex chemical analysis. Both ES and APCI sources interfaced to mass spectrometers can produce ions from continuously flowing liquid samples and hence can serve as on-line detectors for Liquid Chromatography (LC) and Capillary Electrophoresis (CE) separation systems. Liquid samples can also be introduced by continuous infusion or sample injection into a continuously flowing solution. As API/MS systems become easier to operate without compromising performance, less understanding of the technique is required to achieve optimal results. The simpler it becomes to set up and run the API/MS system, the broader the base of investigators who can successfully operate the instrumentation to solve their specific analysis applications. To simplify setup and optimization of the ES and APCI sources, windows have been added to the sides of the ES and APCI chamber which allow viewing inside the API chamber during operation. Optimization and troubleshooting of the Electrospray or nebulization assisted electrospray ban be aided by viewing the spray during operation. A cylindrical lens which extends along the side walls of the atmospheric pressure chamber has been configured to be semitransparent for viewing into the chamber. Improved system sensitivity can be achieved when operating this cylindrically shaped side lens with an elevated potential relative to the Electrospray liquid introduction tube exit tip.

BACKGROUND OF THE INVENTION

Atmospheric Pressure Ionization sources, in particular Electrospray and Atmospheric Pressure Chemical Ionization sources, interfaced to mass spectrometers have become widely used for the analysis of compounds found in solutions. ES/MS system have been described in U.S. Pat. Nos. 4,531,056, 4,542,293 and 4,209,696 the technique and its applications have been reviewed by Fenn et. al., Mass Spectrometry Reviews 1990, 9, 37–70 and by Smith et. al., Mass Spectrometry Reviews 1991, 10, 359–451. Electrospray and APCI have been routinely used as ion sources for on-line LC/MS and CE/MS systems. In Electrospray ionization, as diagrammatically illustrated in FIG. 1, sample bearing liquid is introduced into an atmospheric pressure bath gas through a tube which is generally sharpened at the exit end. A 3 to 6 kilovolt relative potential is applied between the ES liquid introduction tube or needle exit and the surrounding electrodes causing Electrospraying of the sample bearing liquid to occur. Charged liquid droplets formed in the Electrospray process evaporate as they pass through a counter current bath gas in the Electrospray chamber. The charged droplet evaporation leads to Rayleigh disintegration followed by further evaporation and shrinking of droplets. This process eventually leads to the desportion of ions directly from the smaller diameter charged droplet surface into the gas phase. A portion of the atmospheric pressure bath gas, entrained ions and charged liquid droplets are swept into vacuum through an orifice or capillary annulus. When capillaries are used as the orifice into vacuum, the capillary may be heated to further aid in droplet evaporation and ion desportion from the liquid droplets. Ions exiting the capillary enter vacuum through a free jet expansion and are accelerated and focused into a mass analyzer.

Nebulization assist techniques have been applied to Electrospray to extend the range of operation while simplifying its use. High frequency ultrasonic nebulization applied at the Electrospray needle tip has been used to assist the Electrospray droplet formation process. An ultrasonic nebulization assisted electrospray apparatus is manufactured by Analytica of Branford Inc. Alternatively a pneumatic nebulization assisted electrospray has been reported first by Mack et. al. J. of Chemical Physics, 1970, 62 4977–4986 and later in U.S. Pat. No. 4,861,988. Both of these nebulization assisted electrospray techniques have been successful at simplifying operation and improving performance of Electrospray when producing positive or negative ions from liquids entering the Electrospray source with flow rates ranging from less than 1 $\mu$l/min to over 2 ml/min and with a wide range of solution conductivity's and solvent compositions. Unassisted Electrospray has difficulty forming stable sprays for aqueous solutions with higher surface tension, highly conductive solutions and for liquid flow rates over 50 $\mu$l/min. For some applications which require interfacing Electrospray to capillary electrophoresis or in cases where limited sample is available, lower the liquid flow rates may be preferable. The use of unassisted electrospray may yield higher performance for these applications when compared with using nebulization assist techniques. In both assisted and unassisted electrospray methods, it is helpful to observe the spray when optimizing ES source performance. A commercial ES/MS quadrupole mass spectrometer produced by Sciex has used a window located at the end of the cylindrical ES or pneumatic nebulization assisted ES source opposite to the ES endplate or vacuum orifice end. The internal diameter of this ES source is over 7 inches in diameter and the cylindrical side wall is maintained at ground potential. The endplate of this ES source is maintained at a potential within 1000 volts of ground. The window is used to visualize the direction in which a pneumatic nebulizer assisted Electrospray, which produces coarse droplet sizes, is aimed during operation. The position of this viewing window does not allow optimal viewing of the unassisted Electrospray spray. No conductive electrode was placed inside this window to prevent shield the ES source from the effects of space charge buildup on the inside dielectric surface of the window during operation.

The droplet sizes produced by unassisted Electrospray are a function of the liquid flow rate exiting the sharpened Electrospray liquid introduction tube tip. When conserving sample or running microbore fused silica LC columns interfaced to the ES source, the liquid flow rates are typically below 6 $\mu$l/min. For a liquid flow rate of approximately 3 $\mu$l/min, the charged liquid droplet size distribution produced is monodisperse with a mean diameter of 2.93 microns. The Electrosprayed charged droplets fan out due to space charge repulsion as they move away from the needle tip towards the counter electrode endplate. The moving droplets evaporate rapidly in the countercurrent drying gas and decrease in size as they approach the end plate. The droplet diameters produced in the low flow rate Electrospray plume are so small that forward light scattering must be used to observe the spray plume. The Electrospray droplets produced initially can be seen from Mie scattering of visible, but as the droplets evaporate they enter the Rayleigh scattering regime for visible light. A Tyndall color spectra can be observed from a white light source scattered through an Electrospray droplet plume produced from liquid flows of 1 of 2 $\mu$l/min. The quality and stability of the unassisted Electrospray can be quickly ascertained by a direct observation of the spray quality. The present invention includes the incorporation of windows or view ports located in positions around the side walls of an Electrospray chamber. In particular the invention includes windows or view ports which are located on opposite sides of the ES chamber so a light source or viewing angle can be positioned to optimized observed scattering intensity from the ES spray plume. Voltages and needle position can be adjusted to visually optimize Electrospray performance during operation. If the MS signal becomes unstable or decreases, a quick visual observation of the ES plume can determine if the trouble is in the ES spray performance. For example a pulsatile liquid delivery pump or an air bubble emerging at the needle tip will temporarily interrupt the Electrospray process and the lack of spray can be visually observed. The side walls of the ES chamber are conductive to avoid space charge buildup of ions hitting the walls or windows along the side walls of the ES chamber. The conductive side wall electrode, usually cylindrical in shape and extending along most of the sidewall length of the ES chamber, is configured to allow viewing through the electrode into the ES source.

When positive ions are produced in ES sources, the ES liquid introduction tube exit tip is maintained at a positive kilovolt potential relative to the counter electrode endplate and the surrounding cylindrical electrode or lens. When the ES source configuration includes countercurrent bath gas flow, the ES chamber endplate is usually maintained between 0 to 1000 volts above the orifice or capillary entrance potential. The sidewall cylindrical shaped lens potential is usually between 0 and positive 3000 volts relative to the endplate potential in the positive ion operating mode. The direction of the relative potentials would be reversed for the Electrospray production of ions with negative potential. The potentials of the ES chamber electrodes are generally set so that charged entities which leave the ES needle tip are directed and focused by the electrostatic field toward the orifice or capillary entrance into vacuum. In one embodiment of the invention, it was found for some modes of assisted and unassisted ES operation that positive or negative ion signal level can be significantly increased by increasing the potential difference between the cylindrical electrode and the ES liquid introduction tube while maintaining a constant differential between the ES liquid introduction tube and the endplate and capillary entrance electrodes. The mechanism for this increase in sensitivity when an apparent defocusing voltage is set on the cylindrical electrode is not yet clearly understood. The increased sensitivity with increasing cylindrical electrode relative potential appears to be more pronounced at higher liquid flow rates so the defocusing may help to fan out droplets for increased drying efficiency. The increased cylindrical electrode potential relative to the ES liquid introduction needle tip potential may cause an increase in the net charge density per droplet produced resulting in an increase in ES/MS sensitivity.

The inclusion of windows in the sidewalls of an API source and configuring the source chamber to have a semitransparent sidewall electrode which allows viewing of the ES spray and the APCI corona discharge region during operation aids in and simplifies performance optimization and system troubleshooting during operation or either source type. When the side wall electrode is configured to run with a potential difference of up to thousands of volts between the ES liquid introduction needle tip, ES chamber endplate and orifice plate, higher signal intensities can be achieved in unassisted and nebulization assisted Electrospray operation. Increasing ES/MS sensitivity and the improving the convenience of API operation expands the range of applications to which API/MS analysis can be routinely applied.

DESCRIPTION OF THE INVENTION

Figure 1:
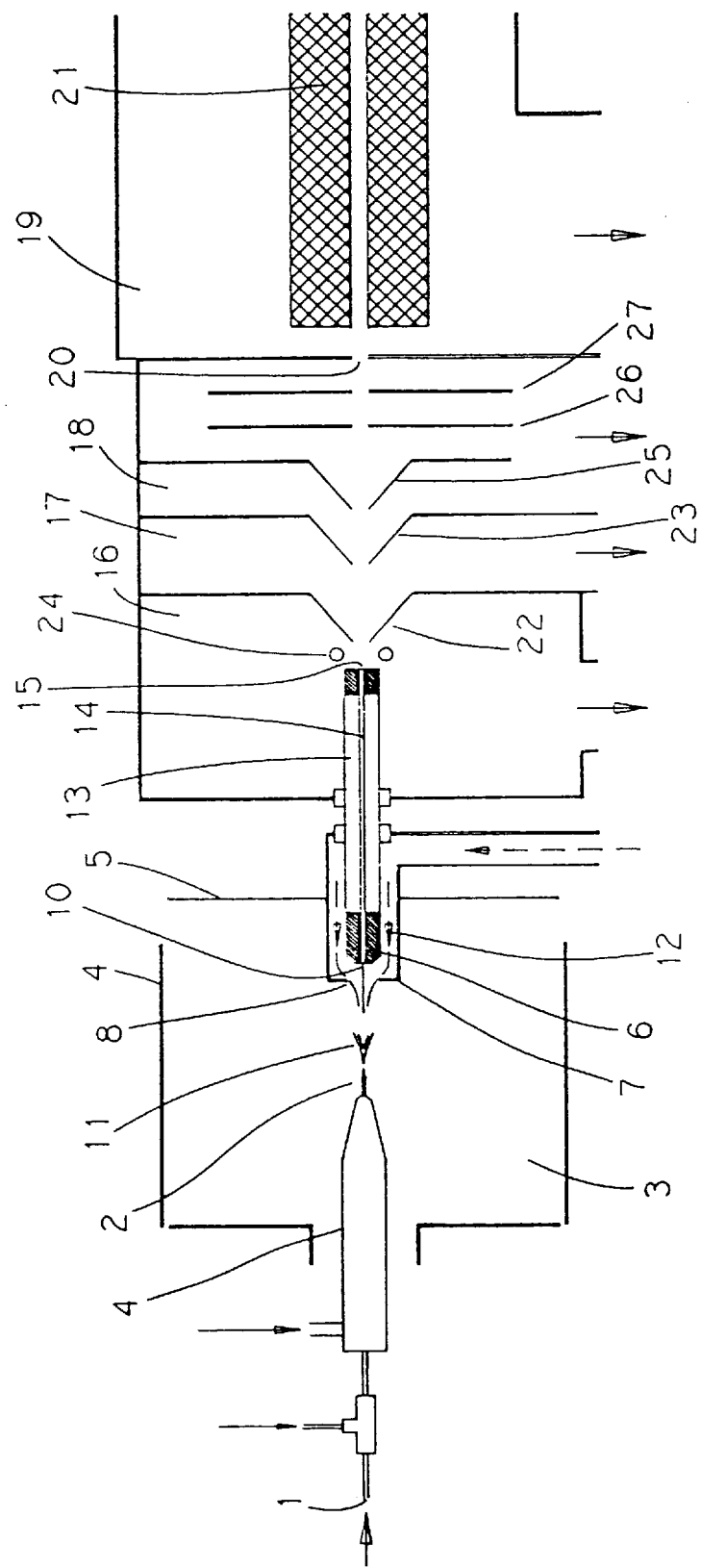
FIG. 1 is a diagram of an Electrospray ion source interfaced to a quadrupole mass spectrometer where four separate voltage elements are present in the ES chamber.

Atmospheric Pressure Sources produce ions at or near atmospheric pressure and deliver these ions into vacuum where they are accelerated and focused into amass analyzer. Electrospray ionization produces charged droplets which, after evaporation, yield ions directly from liquid into the gas phase. In Atmospheric Pressure Chemical Ionization, the sample bearing liquid is first evaporated and sample gas phase ions are produced by chemical ionization charge exchange with solvent ions produced in a corona discharge region located in the atmospheric pressure source chamber. The Electrospray ion source will initially be used as an example to describe the preferred embodiment of the invention. In Electrospray ionization, sample bearing liquid enters tube entrance 1 as shown in FIG. 1 and exits at the sharpened tube or needle tip 2. Electrospray liquid introduction tube tip 2 is maintained at kilovolt potentials relative to surroundings ES chamber 3 electrodes 4, 5, and 6. Electrode 4 is usually cylindrical in shape and extends the length of ES chamber 3. Electrode 5 known as the endplate electrode includes nosepiece 7 to shape electrostatic field lines in ES chamber 3 to achieve more efficient focusing of ions through aperture 8 and into capillary annulus entrance 10. Endplate nosepiece 7 also serves to direct the countercurrent bath gas flow to effect the efficient charged droplet evaporation. The capillary entrance end 6 electrode is operated at a potential difference relative to endplate lens 5 to maximize ion focusing into capillary annulus entrance 10. For solutions and liquid flow rates which fall into the range where unassisted Electrospray can be used, charged droplets are produced by maintaining a potential difference between tube tip 2 and surrounding electrodes 4, 5 and 6 is sufficiently large to cause a Taylor cone to form. The Electrosprayed charged liquid droplets which are produced near needle tip 2 move with the electrostatic field toward endplate nosepiece 7 and capillary entrance 6. The charged droplets fan out to form spray 11 as they move away from needle tip 2. A heated bath gas as indicated by 12, flows countercurrent to the charged droplet movement to aid droplet evaporation. Ions desorb from the evaporating charged liquid droplets and a portion of these ions are swept into vacuum along with neutral bath gas molecules through capillary 13 orifice or annulus 14. Capillary 13 can be heated to aid in droplet evaporation alone or in combination with countercurrent bath gas 12. Shallow orifices have also been used in place of capillary 13 as an entrance into vacuum. Capillary 13 as illustrated is a glass or dielectric capillary with metalized or conductive ends.

Figure 2:
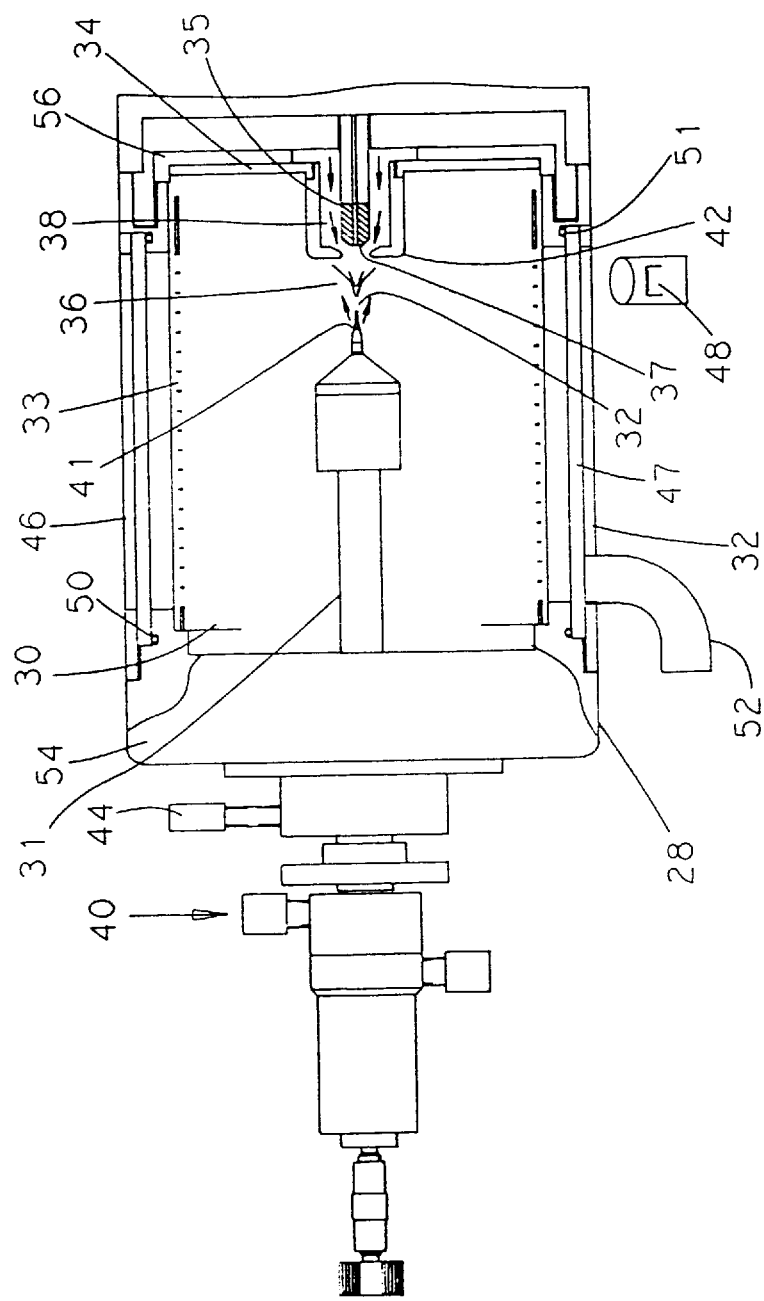
FIG. 2 is a cross section of the Electrospray chamber which includes a semitransparent side wall electrode and windows located on the sides of the ES chamber.

Gas phase ions entrained in the bath gas are swept along in capillary orifice or annulus 14 and enter vacuum through a free jet expansion which forms at capillary exit 15 in vacuum stage 16. Ions are then accelerated and focused through electrostatic ring lens 24, skimmers 22 and 23 and electrostatic lenses 25, 26 and 27 into the mass analyzer entrance aperture 20 while neutral gas is pumped away by vacuum pumping stages 16, 17, 18 and 19. Mass analyzer 21 is illustrated as a quadrupole mass filter, however, this could be a magnetic sector, ion trap, Time-Of-Flight (TOF) or Fourier Transform Ion Cyclotron Resonance (FT-ICR) mass analyzer as well. Four pumping stages have been diagrammed as an example in FIG. 1 but fewer than four or additional vacuum pumping stages can be used with a variety of electrostatic lens configurations to achieve optimal performance for a given mass analyzer. FIG. 2 shows a more detailed cross section view of Electrospray chamber 30 which includes ultrasonic nebulization assisted Electrospray liquid introduction tube assembly 31. Alternatively, assembly 31 could be replaced by a pneumatic nebulization assisted Electrospray liquid introduction tube assembly or an unassisted Electrospray liquid introduction tube assembly. Sample bearing solution exits at the sharpened tube tip 32 which is part of ultrasonic nebulizer assembly 31. During unassisted or nebulization assisted Electrospray operation, tip 32 is maintained at kilovolt potentials relative to ES chamber 30 counter electrodes 33, 34 and 35. The relative voltages are set so that an Electrosprayed spray or plume 36 of charged droplets is driven by electrostatic forces toward the capillary entrance 37 against a heated counter current bath gas 38. If a stable Electrospray droplet formation process can not be maintained because higher liquid flow rates, aqueous of high conductivity solutions are exiting tip 32, then tip 32 can be mechanically vibrated at frequencies over 210 kilohertz to assist the charge droplet formation of the Electrospray process. Additionally focusing gas can be added at fitting 40 and exits through annulus 41 surrounding tip 32. This focusing gas flow can be added to limit the charged droplet drift in the radial direction as they move towards endplate nosepiece 32 and capillary entrance 42. Alternatively, pneumatic nebulization can be used at tip 32 to assist the Electrospray charged droplet formation by increasing the gas velocity exiting annulus 41. With unassisted or nebulization assisted ES a second liquid layer has been added through an annulus surrounding the sample introduction needle tip to modify solution chemistry and improve the ES/MS system performance.

Optimization of the unassisted or nebulizer assisted Electrospray can be aided by observing spray 36 during operation. When Electrospraying a solution where the solution conductivity or percentage of aqueous solvent is unknown, direct viewing of spray 36 with ES chamber electrode voltages applied will determine if stable unassisted Electrospray can be achieved. When low liquid flow rates, typically below 2 µl/min, are used, tip position 32 can be located visually during operation to within 1 cm of endplate nose 42 to achieve maximum sensitivity. If tip 32 shape is irregular, the spray may angle slightly off axis. Viewing of spray plume 36 while adjusting the off axis position of 32 using adjuster 44 allows verification of spray plume direction into aperture 36. When high liquid flow rates are used with nebulization assisted Electrospray, off axis adjustment of tip 32 may be preferred to optimize signal response. Visual confirmation of tip 32 position and spray plume 36 direction during operation simplifies setup and optimization and allows a quick check of the spray quality for troubleshooting purposes. In a preferred embodiment of the invention, windows 46 and 47 have been incorporated into the side walls or the ES source housing 54 to permit viewing of spray 36 during source operation. A light source 48 can be placed to illuminate spray plume 36 by passing light through window 47. With illumination from light 48 shinning through window 47, spray plume 36 can be observed through window 46. For low flow rate Electrospray operation, the droplet sizes produced are small enough to show a Tyndall spectrum from white light scattering through Electrospray plume 36. The angle of viewing must be adjusted to receive the brightest plume 36 image so window 46 and 48 sizes are large enough to allow a range of viewing and illumination angles.

Figure 3:
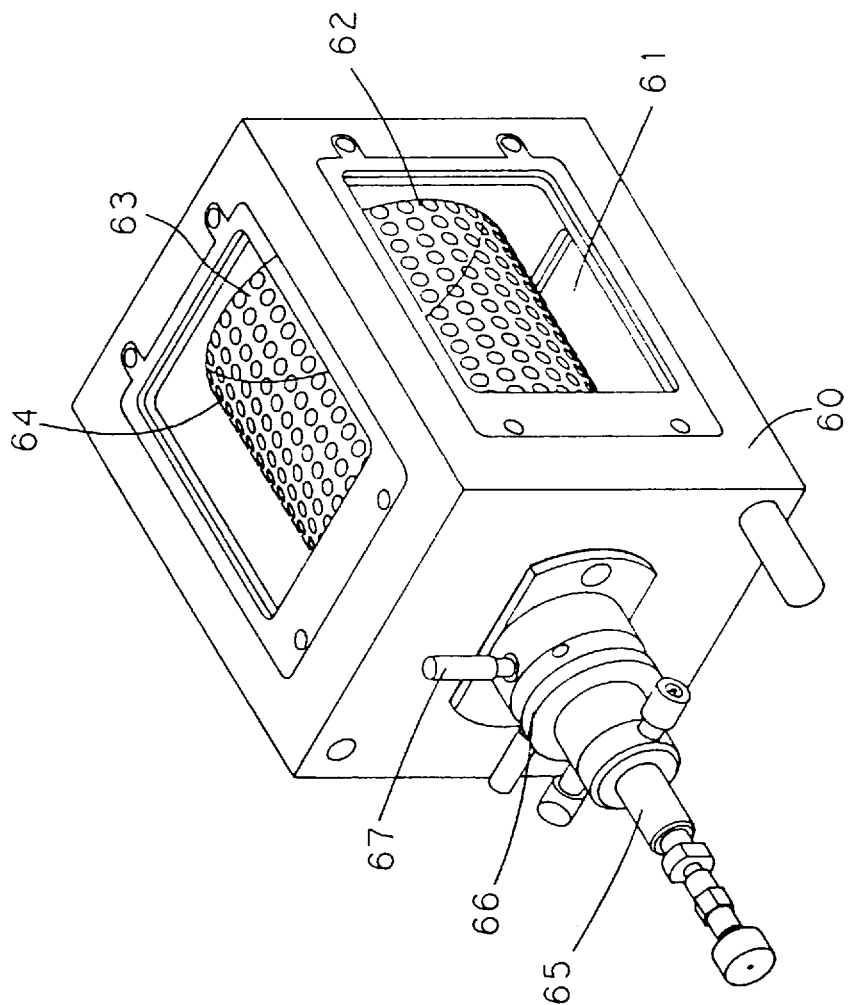
FIG. 3 is an external three dimensional view of the ES chamber with windows located on three sides.

Windows or view ports 46 and 47 are mounted to ES chamber walls and sealed with seals 50 and 51 respectively to prevent gas or vapor form leaking out of ES source 28 during operation. When window 47 is located on the bottom side of ES source chamber 30, window 47 may include a drain or vent port 52. Cylindrical electrode 38 is configured with semitransparent sections for those electrode areas which fall adjacent to windows 46 and 47. Typically 33 is a metal lens configured with screen or perforated sections with transparency over 60% adjacent to windows 46 and 47. The screens or perforated sections of lens 33 allow sufficient optical transparency for viewing but minimize any Electrostatic field penetration into ES source chamber 30 from any external electrostatic fields or charge build up on windows or insulating surfaces outside cylindrical lens 33. In the preferred embodiment shown in FIG. 2, cylindrical lens 33 is electrically isolated from ES liquid introduction tube or nebulizer assembly 31, endplate lens 34 and capillary entrance lens 35 by the dielectric ES chamber housing 54. Endplate lens 34 is electrically isolated from the vacuum housing by insulator 56. This electrical isolation allows the cylindrical lens 33 potential to be set at several kilovolts differential from ES chamber electrodes 32, 34 and 35. ES source chamber 30 outside walls 54 are fabricated from an insulating or dielectric material in the preferred embodiment shown. FIG. 3 is a three dimensional view or ES chamber 60 with viewing windows 61, 62 and 63 located on three sides of ES chamber 60. Cylindrical lens 64 is shown with semitransparent perforated sections adjacent to each window location to allow viewing inside the ES source during operation. ES liquid introduction tube assembly 65 with axial 66 and off axis 67 needle tip 32 adjusters. A light source is typically set to shine through bottom window 61 with the spray 36 observed through top window 63 during ES operation.

When glass or dielectric capillaries are used to transport ions into vacuum as described in U.S. Pat. No. 4,542,293 the ions can climb electrostatic potentials of several kilovolts as they move through the capillary due to the bath gas collisions driving the ions through capillary orifice or annulus 14. With this embodiment, capillary entrance lens 35 can be operated at ground potential and the ES needle assembly maintained at ground potential during operation. Ions entering capillary annulus 14 can be driven uphill against the entrance kilovolt potential by gas collisions and delivered into vacuum at whatever voltage is set on capillary exit electrode 15. Consequently, the dielectric capillary entrance and exit potentials are decoupled and can be set independently of one another. When conductive capillary tubes or orifices are used instead of dielectric capillary 13, the electrostatic potential set on these elements must be set to the voltage required for ion acceleration and focusing into vacuum. Typical ES chamber operating voltages which have previously been reported for positive ion production when ES needle tube tip 32 to endplate nosepiece 42 distance is set at 1.5 cm are given below.

|  | dielectric capillary | conductive capillary or orifice |
| --- | --- | --- |
| ES liquid introduction tube tip 32 | 0 V | +5.0 KV |
| Cylindrical lens 33 | −3.0 KV | +2.0 KV |
| Endplate 34 | −4.0 KV | +1.0 KV |
| Capillary entrance lens 35 | −5.0 KV | +100 KV |

Figure 4A:
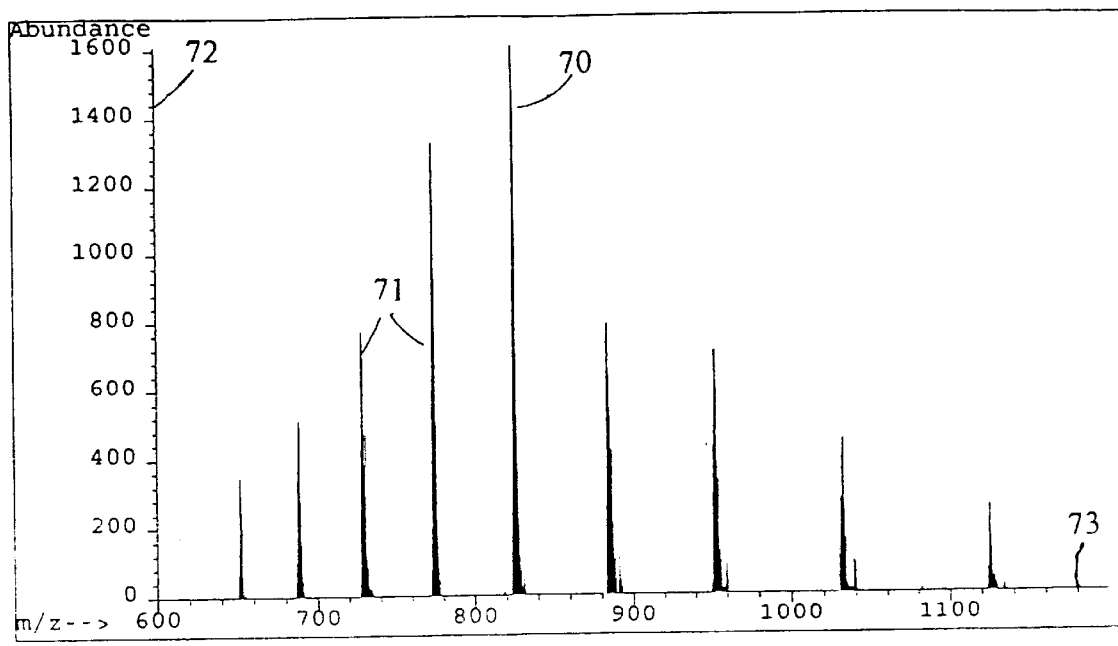
FIG. 4a is an ultrasonic nebulization assisted Electrospray/MS mass spectrum of Cytochrome C taken with a low voltage differential maintained between the cylindrical electrode and the ES liquid introduction needle tip.
Figure 4B:
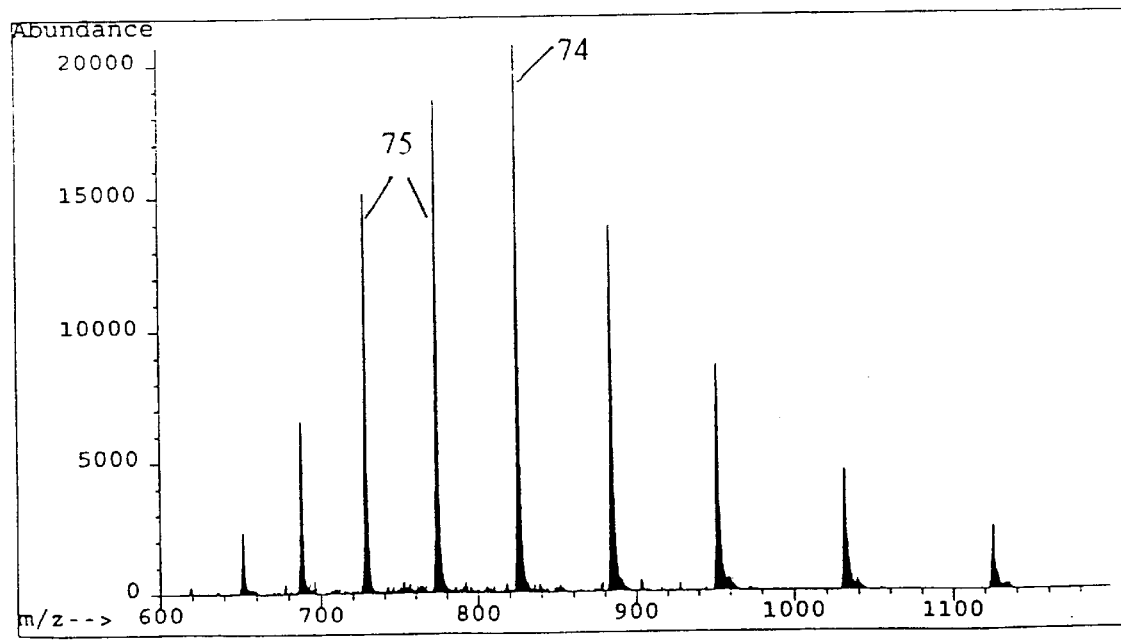
FIG. 4b is an ultrasonic nebulization assisted Electrospray/MS mass spectrum of Cytochrome C taken with a high voltage differential maintained between the cylindrical electrode and the ES liquid introduction needle tip.
Figure 5:
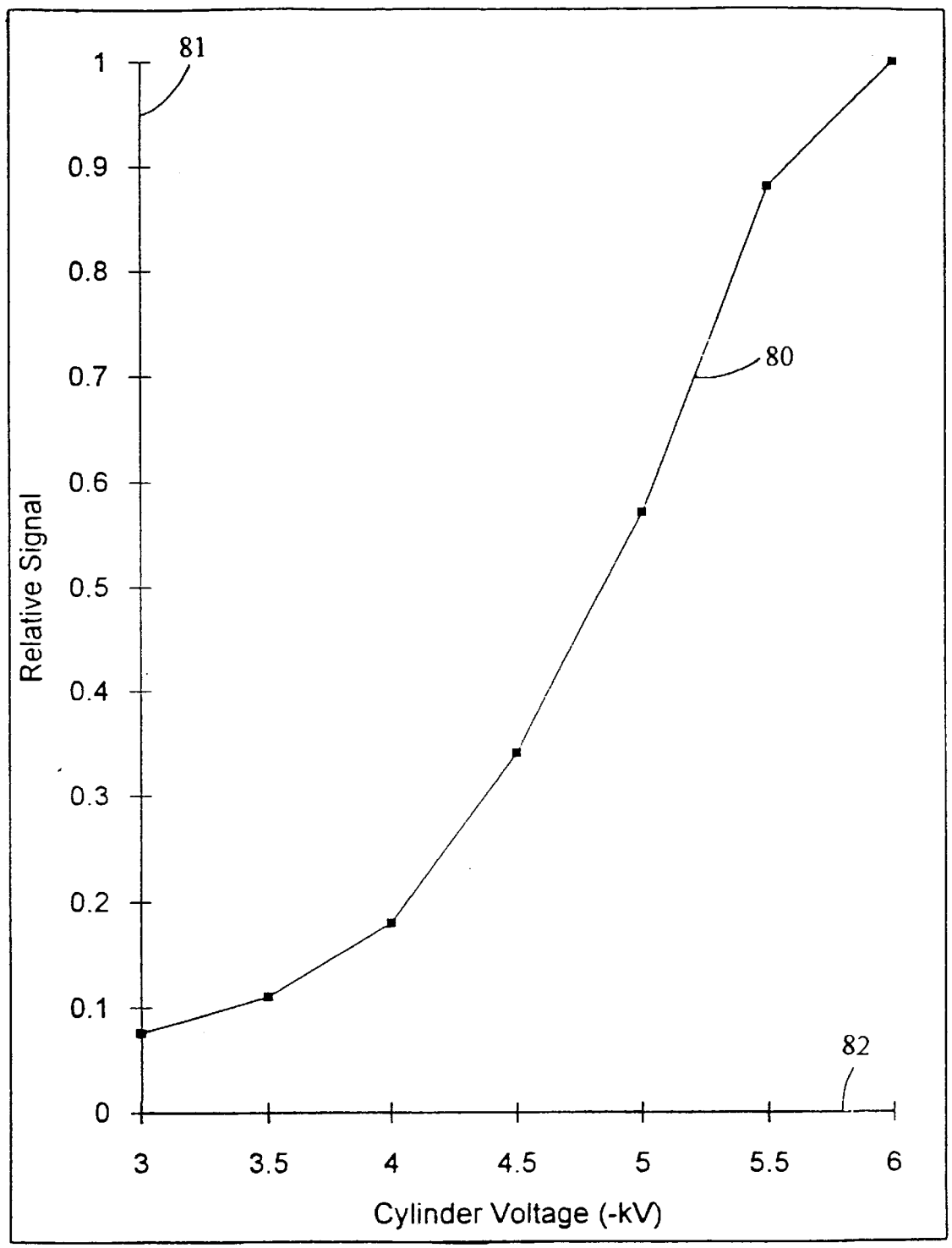
FIG. 5 is a curve of Cytochrome C positive ion signal intensity versus the cylindrical electrode voltage.

For negative ion production, the voltage polarities are reversed. It was discovered that increased ES mass analyzer signal could be attained by increasing the relative cylindrical lens potential 33 to a value greater than that typically used as listed above. FIG. 4a shows an Electrospray quadrupole mass spectrum of Cytochrome C (MW 12360). The spectrum was generated using ultrasonically assisted Electrospray with 200 $\mu$l/min continuous infusion of 1 picomole/$\mu$l solution of Cytochrome C in 1:1 methanol water and 0.1% acetic acid. The ES lens 32, 33, 34 and 35 potentials were set as listed above for a dielectric capillary. The intensity of multiply charged Cytochrome C peaks 70 and 71 shown in FIG. 4a is indicated on Y axis 72 with mass to charge (m/z) ratio given on X axis 73. Note that the $(M+15\ H)^{+15}$ Cytochrome C peak 70 has an amplitude of roughly 1600. FIG. 4b shows a mass spectrum of Cytochrome C where cylindrical lens 33 potential was set a −6.0 KV and all other spray and voltage settings were identical to those set when the mass spectrum in FIG. 5a was taken. Note that the $(M+15\ H)^{+15}$ Cytochrome C peak 74 amplitude has increased to 20,000, a factor of 12.5. The amplitude of related Cytochrome C amplitude peaks 75 has also increased proportionally to m/z peak 74. FIG. 5 shows the relationship 80 between signal intensity of Cytochrome C multiply charged peaks as cylindrical lens 33 potential is increased while holding all other Electrospray variables constant. Signal amplitude is indicated by Y axis 81 with cylindrical lens 33 potential indicated along X axis 82. A significant increase in ion signal is observed as the cylindrical lens 33 potential is increased. The end data points on curve 80 were taken from the mass spectrum shown in FIGS. 4a and 4b. An increase in signal intensity is achieved for both positive and negative ion operating modes when cylindrical lens 33 potential amplitude is increased. Increases in signal intensity can also be observed when pneumatic nebulization is used and cylindrical lens 33 potential amplitude is increased.

It is important to note that because the electrostatic fields inside ES chamber 30 are shielded by lenses 32, 33, 34 and 35 from electrostatic potentials imposed outside chamber 30 the increase in ion signal performance is achieved by setting relative lens potentials in ES chamber 30. Consequently the same Cytochrome C ion signal level observed in FIG. 4b can be achieved by setting the following absolute voltages:

|  | dielectric capillary | conductive capillary or orifice |
| --- | --- | --- |
| ES liquid introduction tube tip 32 | 0 V | +5.0 KV |
| Cylindrical lens 33 | −6.0 KV | −1.0 KV |
| Endplate 34 | −4.0 KV | +1.0 KV |
| Capillary entrance lens 35 | −5.0 KV | +100 KV | because the relative potentials between electrostatic lens elements in Electrospray chamber 30 remain the same for both cases. When Electrospray is operated in an unassisted mode, the effect on signal improvement when cylindrical lens 33 potential amplitude is increased is more pronounced for larger tube tip 32 to endplate nosepiece 42 distances and a liquid flow rate increases. The mechanism for achieving higher signal when increasing cylindrical lens 33 potential amplitude is not yet completely understood. One explanation may be that the higher relative potentials between liquid introduction tube tip 32 and cylindrical lens 33 may result in higher net droplet charge density. At higher liquid flow rates, the higher cylindrical lens 33 potential may help to spread out the charged liquid droplets to achieve more efficient drying for those droplets whose trajectories are along the ES chamber 30 centerline.

Figure 6:
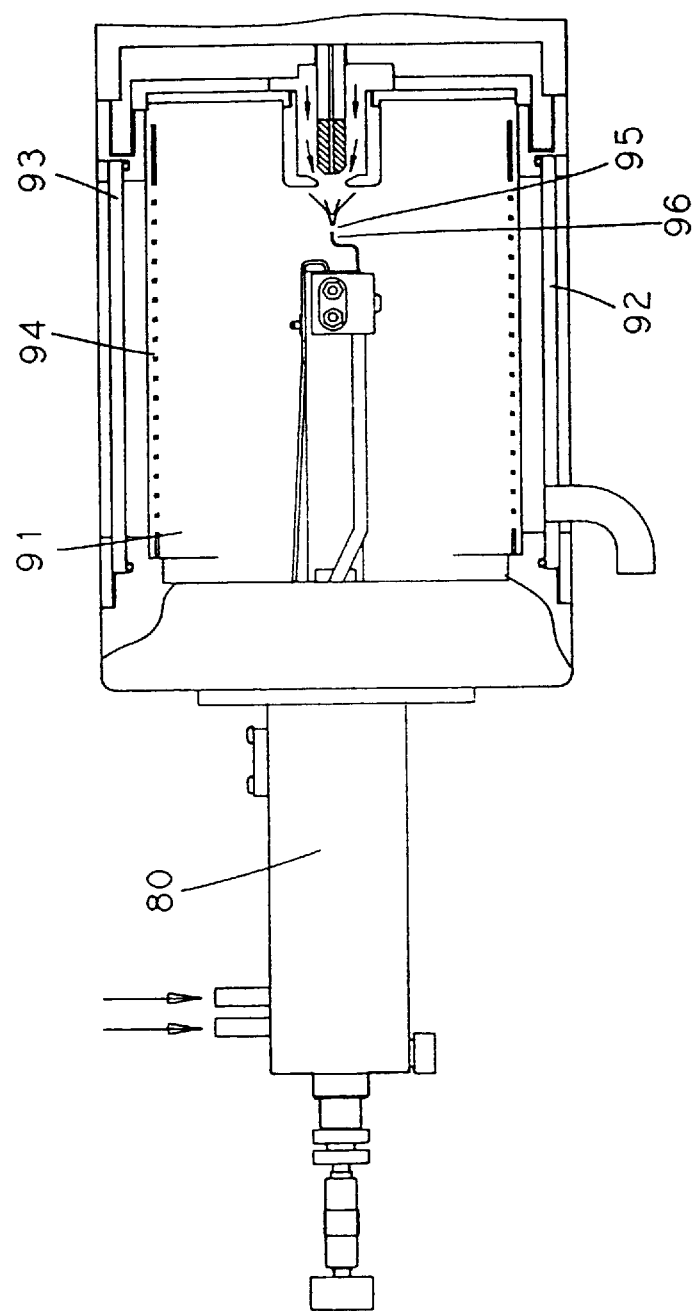
FIG. 6 is a diagram of the APCI probe and corona discharge needle assembly mounted in an atmospheric pressure ion source chamber.

Another embodiment of the invention is shown in FIG. 6 where APCI probe assembly 90 has replaced the ES liquid introduction tube assembly in API chamber 91. The API chamber assembly with windows 93 and 92 and a semitransparent cylindrical lens 94 are similar to the configuration shown in FIG. 2 for ES source assembly 28. The window view ports allow observation of the corona discharge region 95, simplifying troubleshooting and optimization of the corona discharge formed at the tip of sharpened needle 96 during APCI source operation.

We claim:

1. An apparatus for analyzing chemical species comprising:
   a. an Electrospray ion source which produces ions at or near atmospheric pressure from solution and delivers said ions into vacuum through an orifice into vacuum;
   b. said Electrospray ion source includes an Electrospray chamber in which charged liquid droplets of said solution are produced;
   c. a means to deliver said solution into said Electrospray chamber;
   d. one or more view ports located on the sides of said Electrospray chamber;
   g. an electrostatic lens running the length of said Electrospray chamber surrounding said means to deliver said solution into said Electrospray chamber,
   h. said electrostatic lens having semitransparent regions to allow viewing into said Electrospray chamber through said windows,
   i. one or more vacuum pumping stages in vacuum with means for pumping away neutral gas entering vacuum through said orifice with said ions from said Electrospray ion source,
   j. a mass analyzer and detector located in one or more of said vacuum pumping stages to mass analyze said ions which are delivered to vacuum.

2. An apparatus according to claim 1 where said Electrospray chamber includes said view ports located on one side of said Electrospray chamber.

3. An apparatus according to claim 1 where said Electrospray chamber includes said view ports located on opposite sides said Electrospray chamber.

4. An apparatus according to claim 1 where said Electrospray chamber includes said view port located three sides of said Electrospray chamber.

5. An apparatus according to claim 1 where said Electrospray chamber includes said view port which are located on four sides of said Electrospray chamber.

6. An apparatus according to claim 1 where said view port assembly includes a seal.

7. An apparatus according to claim 1 where said mass analyzer is a Time-of-Flight mass spectrometer.

8. An apparatus according to claim 1 where said mass analyzer is a Quadrupole mass spectrometer.

9. An apparatus according to claim 1 where said mass analyzer is a Magnetic Sector mass spectrometer.

10. An apparatus according to claim 1 where said mass analyzer is a Fourier Transform Ion Cyclotron Resonance mass spectrometer.

11. An apparatus according to claim 1 where said mass analyzer is an Ion Trap mass spectrometer.

12. An apparatus for analyzing chemical species comprising:
   a. an Atmospheric Chemical Ionization Source which produces ions at or near atmospheric pressure from solution and delivers said ions into vacuum through an orifice into vacuum;
   b. said Atmospheric Chemical Ionization Source ion source includes an Atmospheric Chemical Ionization source chamber in which charged liquid droplets of said solution are produced;
   c. a means to deliver said solution into said Atmospheric Chemical Ionization Source chamber;
   d. one or more view ports located on the sides of said Atmospheric Chemical Ionization Source chamber;
   g. an electrostatic lens running the length of said Atmospheric Chemical Ionization Source chamber surrounding said means to deliver said solution into said Atmospheric Chemical Ionization Source chamber;
   h. Said electrostatic lens having semitransparent regions to allow viewing into said Atmospheric Chemical Ionization source chamber through said windows,
   i. one or more vacuum pumping stages in vacuum with means for pumping away neutral gas entering vacuum through said orifice with said ions from said Atmospheric Chemical Ionization Source ion source,
   j. a mass analyzer and detector located in one or more of said vacuum pumping stages to mass analyze said ions which are delivered to vacuum.

13. An apparatus according to claim 12 where said Atmospheric Chemical Ionization Source chamber includes said view ports located on one side of said Atmospheric Chemical Ionization Source chamber.

14. An apparatus according to claim 12 where said Atmospheric Chemical Ionization Source chamber includes said view ports located on opposite sides said Atmospheric chemical Ionization Source chamber.

15. An apparatus according to claim 12 where said Atmospheric Chemical Ionization Source chamber includes said view port located three sides of said Atmospheric Chemical Ionization Source chamber.

16. An apparatus according to claim 12 where said Atmospheric Chemical Ionization Source chamber includes said view ports which are located on four sides of said Atmospheric Chemical Ionization Source chamber.

17. An apparatus according to claim 12 where said view port assembly includes a seal.

18. An apparatus according to claim 12 where said mass analyzer is a Time-of-Flight mass spectrometer.

19. An apparatus according to claim 12 where said mass analyzer is a Quadrupole mass spectrometer.

20. An apparatus according to claim 12 where said mass analyzer is a Magnetic Sector mass spectrometer.

21. An apparatus according to claim 12 where said mass analyzer is a Fourier Transform Ion Cyclotron Resonance mass spectrometer.

22. An apparatus according to claim 12 where said mass analyzer is an Ion Trap mass spectrometer.

* * * * *